United States Patent [19]

Lobo

[11] Patent Number: 5,962,239
[45] Date of Patent: Oct. 5, 1999

[54] METHOD FOR DETECTION OF ANTI-HLA ANTIBODIES

[75] Inventor: Peter I. Lobo, Charlottesville, Va.

[73] Assignee: The University of Virginia Patent Foundation, Charlottesville, Va.

[21] Appl. No.: 08/852,095

[22] Filed: May 6, 1997

Related U.S. Application Data

[60] Provisional application No. 60/016,955, May 6, 1996.

[51] Int. Cl.$^6$ ................................................. G01N 33/533
[52] U.S. Cl. .................... 435/7.24; 435/7.1; 435/7.94; 435/23; 435/40.52; 436/507; 436/175; 436/176; 436/811; 436/825
[58] Field of Search ..................................... 435/7.1, 7.24, 435/7.94, 23, 40.52; 436/507, 175, 176, 811, 825

[56] References Cited

PUBLICATIONS

Lobo et al., Transplant International, vol. 8, No. 6, pp. 472–480, 1995.

*Primary Examiner*—Christopher L. Chin
*Assistant Examiner*—Bao-Thuy L. Nguyen
*Attorney, Agent, or Firm*—Oblon, Spivak, McClelland, Maier & Neustadt, P.C.

[57] ABSTRACT

An improved method for detecting even low titer HLA antibodies in proposed organ transplant recipients employs flow cytometry crossmatching (FCXM) on pronase-treated B-cells and T-cells of the donor. Two-color FCXM is preferably employed. The peripheral blood lymphocytes, after pronase digestion, are maintained under conditions to suppress Fcy R receptor regeneration, combined with sera of the proposed transplant recipient, and tested against control sera, using fluorescent reporting complexing agents. Use of pronase digested lymphocytes permits the assay to distinguish between normal or irrelevant IgG B cell binding and immunologically important HLA antibody binding.

5 Claims, 2 Drawing Sheets

METHOD FOR DETECTION OF ANTI-HLA ANTIBODIES

This application is a regular National application claiming priority from Provisional Application, U.S. application Ser. No. 60/016,955 filed May 6, 1996.

FIELD OF THE INVENTION

This invention pertains to a method for the detection of anti-Human Leukocyte Antigen antibodies (anti-HLA antibodies) in projected organ transplant recipients. Specifically, a method for detecting low titer anti-HLA antibodies, which precipitate rejection syndrome is provided. The method is both selective in nature, and objective in operation. A high degree of sensitivity is obtained. The method is particularly useful in detecting weak titers in retransplant recipients, and particularly valuable in the assessment of potential kidney, heart, lung, pancreas and all solid organ transplant recipients.

BACKGROUND OF THE INVENTION

Organ transplant rejection syndrome is well documented. In this situation, organs transplanted to a recipient from a donor are bound by antibodies circulating in the blood of the recipient, that is, anti-HLA antibodies. Organ rejection leads to loss and destruction of the transplanted organ, and acute medical and pathological problems for the recipient.

Two assays have been developed in the art to ascertain the presence of donor-specific antibodies in proposed transplant recipients. In one assay, a compliment-dependent microcytotoxicity assay (CDL) using peripheral blood lymphocytes (PBL) of the donors is employed. This technique is well documented, and, in the case of renal transplants, employs a modified Amos technique. Polymorphs and macrophages are separated off, and mononuclear cells may be further purified with T-B Kwik (one lambda, California). This prior art assay method calls for incubation of cells with sera (from the proposed recipient) at 25° C. for 30 minutes, the cells being washed twice and then incubated with goat anti-human kappa for 2 minutes before adding rapid compliment at 25° C. for 1 hour. Cell death is determined by eosin staining followed by formalin fixation. As an alternative assay, indirect immunofluorescence (IF) assays have been previously developed. The inventor, working together with others, developed this technique (IF) to increase sensitivity and specificity of the assay. Lobo et al., Transplantation 23:16–21 (1977). This assay was particularly characterized by pre-digestion of the donor lymphocytes with pronase to remove Fcγ R receptors that bind to the Fc region of normal or irrelevant IgG. This is a requirement to avoid false negative assays, as it is impossible to distinguish binding of normal or irrelevant IgG from anti-HLA binding. See, Lobo et al., J. Immunol. 117:939–942 (1976) and Lobo et al., Hum. Immunol. 1:55–60 (1981).

IF assays proved to be difficult in a clinical environment, however, in part due to the requirements for ultraviolet microspy (X800 magnification) which renders the test highly subjective, and cumbersome.

In 1983, an improved method for detecting anti-HLA antibody binding to donor lymphocytes was developed, employing flow cytometry instead of microscopy to quantitate antibody binding. Garovoy et al., Transplant Proc. 15:1939–1945 (1983). This assay, or flow cytometric crossmatch (FCXM) has received broad attention in the art. In FCXM, using normal control sera and donor sera, a fluorescence histogram is obtained. A curser is set at the point on the histogram where most or all of the cells to the left of the curser are considered to be fluorescent-negative. A serum that increases fluorescence to the right of the curser is considered positive. Given the presence of receptors that bind to normal or irrelevant IgG in normal patient sera, however, it has been found difficult to differentiate IgG binding, and to identify sera that are truly negative for anti-HLA antibodies. Thus, the FCXM assay developed lacks specificity.

In an attempt to answer this lack of specificity, a two-color system was developed, where T or B or lymphocytes were identified with phycoerythrin-labeled anti-T or -B murine monoclonal antibodies, to avoid binding results of irrelevant or normal IgG on the non-B, non-T-lymphocyte subset. This technique continues to experience "false-positive" problems. Ogura et al., Transplantation 56:294–298 (1993) and Scornik et al., Transplantation 57:621–625 (1994).

Thus, although superior to CDL in identifying anti-HLA antibodies in the sera of proposed organ recipients, FCXM lacks specificity. IF, on the other hand, is cumbersome and subjective.

Retransplant recipients pose a special problem for detection of low titer (or weak) HLA class I antibodies that bind only to B cells. These recipients typically have high T cell panel reactive antibodies (PRA).

Thus, it remains an object of those of ordinary skill in the art to develop an assay that is objective, sensitive and specific, that will allow the reliable detection of anti-HLA antibodies in proposed transplant recipient patients, and avoid problems of both false positive and false negative results.

SUMMARY OF THE INVENTION

The above objects, and others made evident by the discussions set forth below, are met by a highly sensitive and specific assay for the detection of anti-HLA antibodies, which specifically provides means for detecting donor-specific HLA class I antibodies reactive only to B cells.

In the improved method, donor lymphocytes are isolated and separated, and subsequently treated with pronase to remove Fcγ R receptors on the lymphocytes. The enzymatically treated cells are kept at 4° C. in the presence of sodium azide or other receptor regenerator inhibitor so as to prevent a regeneration of Fcγ receptors which typically occurs if incubated at room temperature or above in a culture medium without sodium azide. As pronase digestion does not remove HLA and CD3 antigens, the pronase-digested lymphocytes are combined with sera and subjected to conventional two-color flow cytometric crossmatching. See, Bray et al., Transplantation 48:834–840 (1989) incorporated herein by reference.

Unlike prior flow cytometric crossmatching, even two-color flow cytometric crossmatching, the process of the claimed invention, which includes pronase digestion of the PBL prior to assay, permits detection of weak anti-HLA class I antibodies that are only reactive to donor B lymphocytes. This is due to the fact that in non-pronase digested PBL, normal IgG binding to the Fcγ R receptors on B cells cannot be distinguished from IgG anti-HLA binding.

BRIEF DESCRIPTION OF THE FIGURES

Legend to FIG. 1

Donor PBL were incubated with human sera for thirty minutes at 4° C., washed twice and then re-incubated with FITC goat F(ab$^1$)$_2$ anti-human IgG at 4° C. for thirty minutes. After three more washes, the cells were incubated with PE-anti CD19 at 4° C. for thirty minutes and washed four times prior to two color FCXM. All sera used were centrifuged at 10,000 g. Four control AB sera were used.

Figure 2:
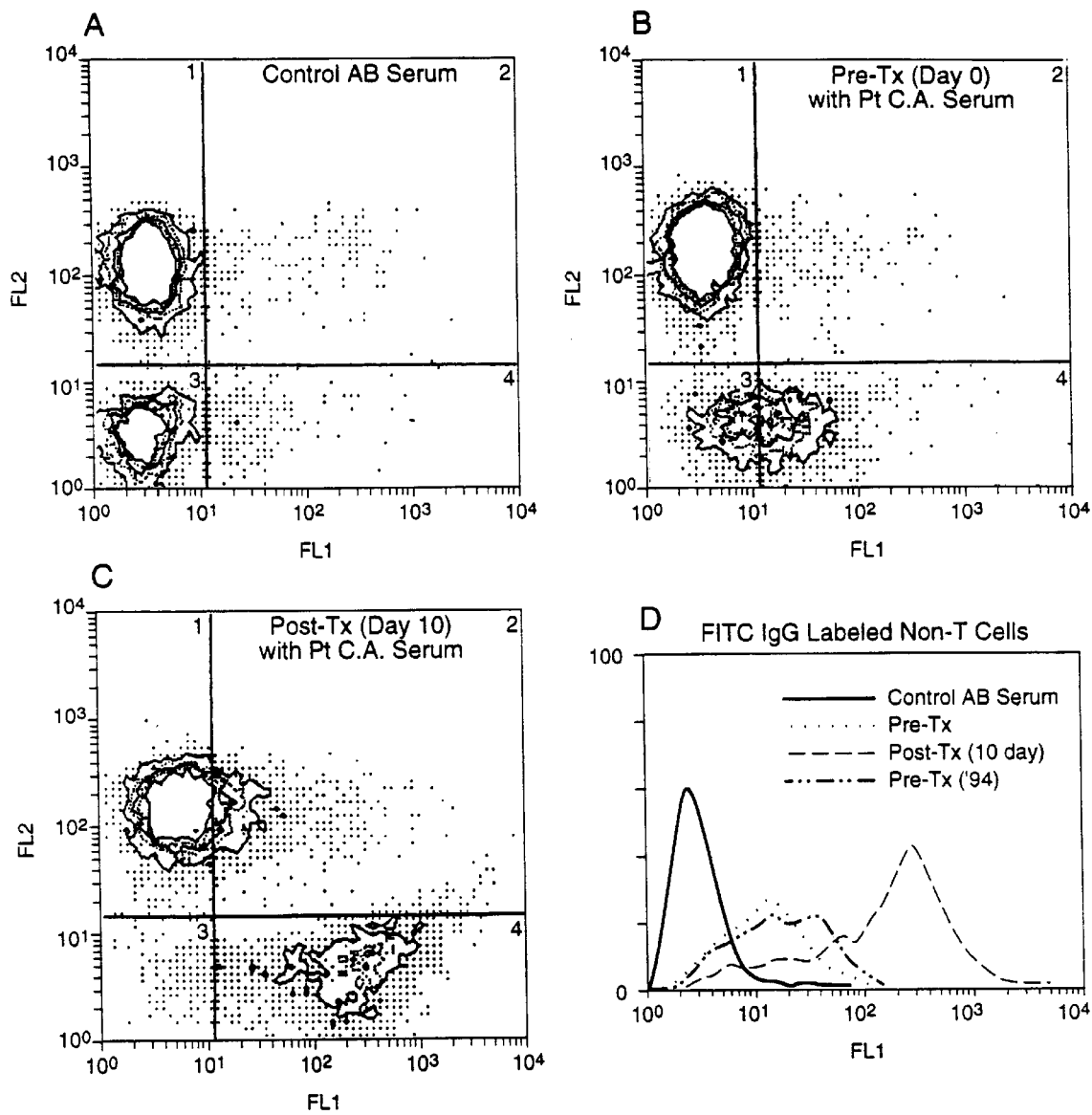

Legend to FIG. 2

Figure 1:
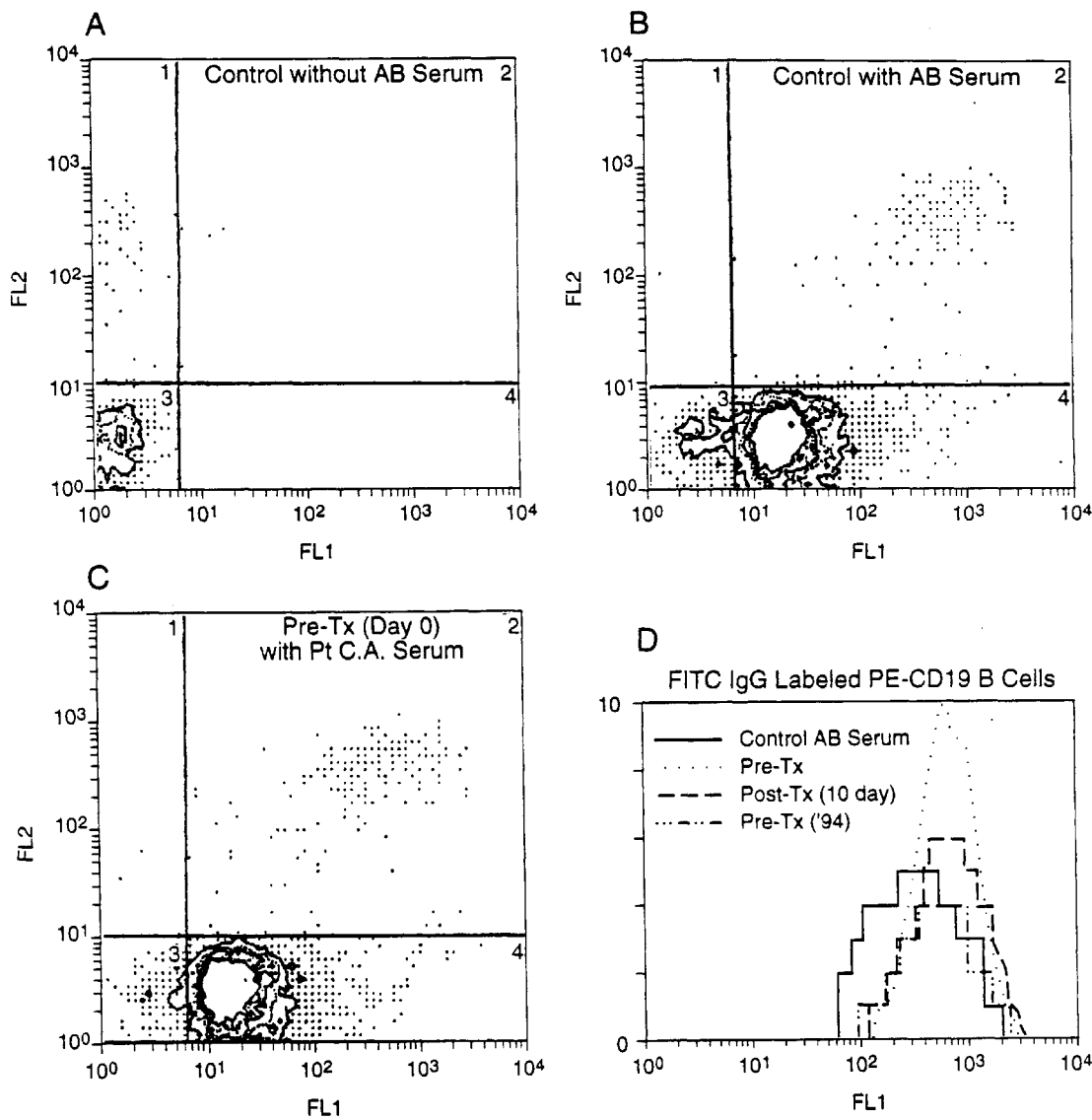
FIG. 1B is a representative example of one of these control AB sera. Since the donor had 3 to 4% CD19 positive B cells, there are very few double stained cells in quadrant #2 of FIG. 1B and FIG. 1C.
FIG. 1D depicts the FITC histograms after analyzing quadrants #1 and #2. Note that there is strong IgG binding to B cells with both AB serum and patients sera (pre and post transplant accordingly, FIG. 1A is a control without the addition of AB sera, FIG. 1B is reflective of the control with AB sera, FIG. 1C reflects the addition of patient serum and FIG. 1D is the FITC histogram of quadrants one and two of the figures).

Donor PBL were initially pronased to remove Fcγ R (5) prior to interacting with sera. Sera and conjugates were interacted with PBL as in FIG. 1. However, in this figure we examined binding of FITC labeled IgG to non-T cells since PBL were stained with PE-anti CD3. Quadrants #3 and #4 are analyzed for FITC IgG binding to non-T cells in the histogram of FIG. 2D. Note that control AB serum had very low background IgG binding and, hence, it was easy to identify FITC IgG binding to non-T cells in pre-transplant sera, accordingly, FIGS. 2A–2D reflect FCXM in a sequence similar to FIGS. 1A–1D, where the PBL were pronased to remove Fcγ R.

DETAILED DESCRIPTION OF THE INVENTION

As noted, it is not uncommon to encounter situations of low titer (or weak) HLA class I antibodies that bind only to B cells in proposed transplant recipients. This is particularly true in patients proposed for retransplantation with high levels of T cell reactive antibodies. There is general agreement that transplantation should be avoided in patients with HLA class I antibodies specific for B cells. Phelan et al., Transplant Proc. 21:687–688 (1989) and Scornik, Transplantation 54:61–64 (1992). Thus, detection of these antibodies in proposed recipients is of paramount importance. This is true of kidney, heart, lung, pancreas and all solid organ transplants. While IF is a highly sensitive and specific process, very few laboratories employ this technique. The microscopy required is subjective and is dependent on the involved technologists' skill and experience. Additionally, with IF, examination of about 300 cells is the maximum. In contrast, flow cytometry crossmatching, which examines up to 10,000 cells in one pass, offers an objective, easily read measure. Even two-color FCXM, however, is not sufficiently specific to detect weak HLA antibody specific for B cells. This is demonstrated in the case description set forth below.

Pronase digestion, which removes Fcγ R receptors allows the fluorescence histogram reviewer to identify even extremely low titer anti-HLA antibodies specific for B cells. While use of pronase digestion had been demonstrated to be effective in conjunction with IF, Lobo et al., Transplantation 23:16–21 (1977), this method proved, ultimately, to be unsatisfactory for clinical analysis. Most skilled artisan were concerned that pronase digestion would alter the cells themselves, rendering them unfit for FCXM.

Using conventional flow cytometry crossmatching techniques, the sensitivity of this assay, particularly in two-color FCXM, can be retained, and specificity improved by pronase digestion. In this process, peripheral blood mononuclear cells are isolated from the donor through conventional Ficoll-hypaque methods. These are further purified with T/B Lymphokwik™ (One Lambda).

The cells are combined with human sera, incubated for a brief period (15–60 minutes) and then reincubated with, e.g., FITC goat anti-human IgG, and then subsequently, incubated with a derivitizing conjugate such as PE-Leu. After washing, flow cytometric crossmatching is performed. (An exemplary instrument for measuring the conjugated anti-CD3 reagent obtained from Beck and Dickenson is a FAC scan, equipped with a Consort 30 computer program). In its broadest embodiment, then, this invention requires separation of lymphocytes from the donor, combination with the sera of the proposed transplant recipient, combination and binding with anti-sera and conjugation with a fluorescent reporter agent. Preferably, two-color flow cytometry is employed. These processes are known to those of skill in the art, and are described, e.g., in U.S. Pat. No. 5,064,616, as well as the literature cited above. The light emitted by the tagging or reporting agents is provided in the form of a fluorescence histogram, compared against control sera, to give a binding count. Without pronase digestion, binding to receptors on the donor lymphocytes occurs with non-HLA antibody IgG. Thus, pronase receptor digestion is essential for specificity. While any digestion agent selective for Fcγ R receptors is satisfactory, the pronase enzymes from *Streptomyces griseus*, from a variety of commercially available sources, can be employed. Type four enzymes, used in prior studies, including Windfield, et al., J. Immunol. 119:1778–1784 (1977), Type VI, Lobo et al., 1977, supra and type III enzymes have been demonstrated to be suitable.

Pronase digestion, by any suitable protease, following conventional methodologies. The enzyme is diluted, incubated with the separated lymphocytes at 35–40° C. for 15–60 min., washed thoroughly and maintained as indicated, under conditions which suppress regeneration of Fcγ R receptors, e.g., 4° C. in a sodium azide culture. This preserves cell viability (over 85%) removes Fcγ R receptors, but does not affect HLA and CD3 antigens.

It should be noted that these results, including the case studies set forth below, have been reported in non-prior art literature, the work of the inventor, as reported in Lobo et al., Transplant. Int. 8:472–480 (1995).

Case Study

C. A. is a 37-year-old Caucasian female with end stage renal disease (ESRD) secondary to hypertension. She received a cadaveric renal transplant in August 1991, with the following HLA match; Donor A3, A11, B35, B51, DR4, DR13, DQ6, and DQ7, recipient A2, A25, B18, B51, DR11, DR13, DQ6 and DQ7. Recipient C. A. developed irreversible rejection and began dialysis five weeks post transplant. During the five weeks post transplant, patient developed two episodes of acute cellular and vascular rejections unresponsive to two courses of Solu-Medrol taper and OKT3. Patient did not undergo transplant nephrectomy. Five months post transplant she developed anti-HLA class I and II antibodies reactive to frozen donor cells and to a panel of B and T lymphocytes from random donors (T cell PRA=47%, B cell PRA=58%). The B cell PRA was performed after absorbing sera with platelets. Antibody had specificity to HLA A1, A3, A11, B35, DR4 and DR7. Her PRA reactivity to T cells declined over ten months and on September 1995 she received a second kidney transplant donated by her brother. It was a one haplotype match and the mismatched antigens were B55 and DR9. The pre-transplant cross-match assays (see below for the assays used) with donor peripheral blood lymphocytes were negative with sera one day pre-transplant and also with sera 3, 6 and 12 months pre-transplant. Their respective T cell PRA were 96, 77, and 69%. Patient became anuric within one hour post transplant and 48 hrs later she underwent donor nephrectomy, and found to have classical changes of hyperacute rejection on histology of her allograft. Anti-donor IgG antibody to T and B cells were detected by both cytotoxicity and indirect immunofluorescence assays from sera 48 hours post transplant.

Pre-transplant Cross-Match Assays

Ficoll-Hypaque separated mononuclear cells were obtained from donor blood. Contaminating polymorphonuclear cells and macrophages were removed by T-B Kwik (One Lambda, Canoga Park, Calif.). As is routine in our laboratory, two assays were used-pre-transplant to detect donor-specific antibodies, (i) a compliment-dependent micro cytotoxicity assay (CDL) using peripheral blood lymphocytes (PBL) (CDL was performed according to the modified Amos technique with antiglobulin and PBL contained both T and B cells; Sera used were DTT pre-treated to remove IgM antibodies), and (ii) indirect immunofluorescence (IF) with PBL that were pronase digested to remove FcγR on lymphocytes. Digested cells were interacted with sera at 4° C., washed and then stained with FITC conjugated goat anti-sera specific for either IgM or IgG prior to enumerating the percent of FITC positive cells by phase-contrast immunofluorescence microscopy. Both techniques are described in detail elsewhere. Lobo, 1981, supra and Lobo, 1995, supra.

Using both assay systems patient C. A. was found not to have donor-specific T cell IgG antibodies in her current and previous sera. Reactivity of IgG antibody to B cells was determined by IF in our laboratory. IgG antibody to B cells is considered to be present when the percent of lymphocytes staining for IgG are similar to the percent of B cells. However, with patient C. A. sera it was difficult to determine by IF whether there was indeed a B cell antibody as PBL from her donor had between 3–4 percent B lymphocytes and 3 to 4 percent of IgG staining was observed with patient C. A. sera. This value was not significantly different from background staining using control AB sera. As a rule, detection of B cell IgG antibody by IF is not a problem as in peripheral blood most donors have been 9 to 15 percent B cells and background IgG staining is not more than 3 percent.

Retrospective Analysis of Pre-Transplant Sera

Loss of the allograft by hyperacute rejection prompted us to reexamine her pre-transplant sera by two color FCXM and also by performing a donor-specific CDL assay on enriched B cells. Two color FCXM was performed by routinely described techniques using PBL subjected to T-B Kwik. In addition, we repeated the two color FCXM using pronase digested PBL. Both techniques have been described in detail elsewhere. Bray, 1989, supra and Lobo, 1995, supra. The latter technique improves specificity without altering sensitivity.

No antibody binding to T cells could be detected in patient C. A. sera with either non-pronased or pronased PBL using two color FCXM. However, as can be observed from FIG. 1, there was no significant difference in IgG binding to CD19 B cells between control AB sera and patient C. A. sera when using non-pronased PBL in the two color FCXM. In fact, IgG from all 4 control AB sera that we tested bound to B cells making it difficult to determine if patient C. A. indeed had a B cell specific antibody pre-transplant. In FIG. 2, pronased PBL were used in two color FCXM. PBL were stained with pycoerythrein (PE) conjugated anti-CD3 antibody. Data from FIG. 2 clearly demonstrates that patient C. A. sera, but not control AB sera, had an IgG antibody that bound to non-T cells. Binding to pronased non-T cells could not be demonstrated after using pre-transplant sera absorbed onto platelets. Sera obtained two and ten days post transplant clearly had antibody binding to T cells that could be detected by CDL, IF and two color FCXM (using non-pronased cells). Such findings would support the concept that the patient pre-transplant had a low titer donor-specific HLA class I antibody that bound only to B cells.

In separate studies, donor B cells were positively selected from PBL with Dynabeads HLA class II (Dynal Inc., Norway). Vandel et al., Issue Antigens 28:301–312 (1986). CDL was performed with recipient pre-transplant sera using donor B cells. The donor-specific B cell cross match was positive with pre-transplant sera at a dilution of 1:4 utilizing the Amos modified CDL assay. These findings confirmed our observations using pronased PBL with the two color FCXM.

Discussion

Since one third of transplant recipients are retransplants with high T cell PRA, it is not uncommon to encounter situations of low titer (or weak) HLA class I antibodies that bind only to B cells. As a rule two approaches are used for detection of B cell donor-specific antibodies, (i) a CDL assay using highly enriched B cells separated from PBL and (ii) two color FCXM with PE-conjugated CD19 or IF as we do in our laboratory. It is necessary to use FCXM (or IF) in addition to CDL as weak HLA class I antibodies to B cells may be non-detectable by the CDL assay and only be detected by IF or FCXM. Early renal allograft loss has occurred in the presence of HLA class I antibodies that failed to be detected by CDL on B cells.

This case serves to illustrate the lack of sensitivity with currently used two color FCXM, especially when identifying IgG antibodies reactive only to B cells. Two color FCXM was introduced on the assumption that CD19 B cells and T cells did not have FcγR receptors capable of binding to normal or irrelevant IgG present in control AB serum. Unfortunately, this is not the case. Hence, one cannot differentiate between binding of normal IgG to Fcγ R on B cells and binding of IgG to the HLA antigens on B cells (See FIG. 1). Based on the same premise, it can also be difficult to differentiate between binding of weak anti-HLA class I antibodies and normal IgG to Fcγ R on T cells. Consequently, two color FCXM lacks specificity. Between 70 to 90 percent of patients had a positive two color FCXM and would have been denied a kidney transplant if the decision to transplant had been solely based on FCXM, using non-pronased PBL. Ogura et al., 1993, supra.

To circumvent this problem, we used pronase digested lymphocytes in the two color FCXM. Pronase digests Fc yR, but does not digest HLA and CD3 antigens. This case clearly illustrates that with two color FCXM and non-pronased PBL, one could have failed to detect the anti-HLA class I antibody that only reacted to B cells. Data in FIG. 2 clearly illustrates that pronase digested PBL improves sensitivity and specificity of two color FCXM, especially with an IgG antibody reactive to B cells. This is particularly relevant in situations when the B cell specific anti-HLA antibody is too weak to be detected by CDL and yet can cause graft loss within the first week. Secondly, with pronased PBL, one can expedite FCXM. By using PE-conjugated anti-CD3, one can simultaneously identify binding of IgG to pronased T or non-T cells (FIG. 2). Pronase digestion removes Fc γR present on non-T cells (i.e., B and NK cells). Hence, one does not have to repeat the two color FCXM with PE-labeled B cells.

Applicants' invention has been described generically, and by reference to specific example. Alternatives and modifications will occur to those of ordinary skill in the art without the exercise of inventive faculty. In particular, specific blood separation protocols, digestion methods, reporter molecules and the like will occur to those ordinary skill in the art without the exercise of inventive faculty. These alternatives remain within the scope of the invention, save as excluded by the recitations of the claims set forth below.

What is claimed is:

1. A method for detecting Human Leukocyte Antigen (HLA) antibodies in the blood of a mammal, which antibodies are reactive with donor tissues from a donor, comprising:

isolating lymphocytes from said donor, enzymatically digesting Fcγ R receptors of said lymphocytes and maintaining said treated lymphocytes under conditions which suppress regeneration of said receptors, combining said treated lymphocytes with sera from said mammal, and conjugating any antibody-bound material with a fluorescent reporting agent to obtain a test sample, subjecting said test sample to flow cytometry crossmatching to obtain an image of detected fluorescence, and analyzing said image to determine the presence of HLA antibodies.

2. The method of claim 1, wherein said HLA antibodies comprise low titer HLA class I antibodies that bind only to B cells.

3. The method of claim 1, wherein said flow cytometry crossmatching is two-color flow cytometry crossmatching.

4. The method of claim 1, wherein said donor tissue comprises renal, heart, lung, liver or pancreatic tissue.

5. The method of claim 1, wherein said step of enzymatically digesting comprises treating said donor lymphocytes with pronase.

* * * * *